United States Patent
Yang et al.

(10) Patent No.: US 8,507,747 B2
(45) Date of Patent: Aug. 13, 2013

(54) ABSORBENT ARTICLE

(75) Inventors: Qiye Yang, Kagawa-ken (JP); Koichiro Mitsui, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 618 days.

(21) Appl. No.: 12/517,138

(22) PCT Filed: Nov. 8, 2007

(86) PCT No.: PCT/JP2007/071711
§ 371 (c)(1),
(2), (4) Date: Jun. 1, 2009

(87) PCT Pub. No.: WO2008/072433
PCT Pub. Date: Jun. 19, 2008

(65) Prior Publication Data
US 2010/0057030 A1    Mar. 4, 2010

(30) Foreign Application Priority Data

Dec. 12, 2006    (JP) ................. 2006-335055

(51) Int. Cl.
*A61F 13/15*    (2006.01)
(52) U.S. Cl.
USPC ............ 604/380; 604/378; 604/370; 604/372
(58) Field of Classification Search
USPC .......................... 604/366, 370, 372, 378, 380
See application file for complete search history.

(56) References Cited

U.S. PATENT DOCUMENTS

| | | | |
|---|---|---|---|
| 1,863,333 A * | 6/1932 | Heitmeyer ................. 604/380 |
| 3,494,362 A * | 2/1970 | Burgeni ..................... 604/374 |
| 6,372,954 B1 * | 4/2002 | Johnston et al. ........... 604/378 |
| 2004/0243079 A1 * | 12/2004 | Mitsui et al. .............. 604/367 |
| 2004/0265534 A1 * | 12/2004 | Curro et al. ................. 428/92 |
| 2005/0025964 A1 * | 2/2005 | Fairbanks et al. ......... 428/364 |
| 2005/0148964 A1 * | 7/2005 | Chambers et al. ......... 604/367 |
| 2005/0177122 A1 * | 8/2005 | Berba et al. ................ 604/367 |
| 2006/0100598 A1 * | 5/2006 | Tamura et al. ............. 604/380 |

FOREIGN PATENT DOCUMENTS

| | | |
|---|---|---|
| JP | 11-137600 A | 5/1999 |
| JP | 2001-309945 A | 11/2001 |
| JP | 2002-011047 A | 1/2002 |
| JP | 2004-285549 A | 10/2004 |
| JP | 2006-297070 A | 11/2006 |

OTHER PUBLICATIONS

International Search Report of Application No. PCT/JP2007/071711 mailed Jan. 8, 2008.

* cited by examiner

*Primary Examiner* — Lynne Anderson
(74) *Attorney, Agent, or Firm* — Lowe Hauptman Ham & Berner, LLP

(57) ABSTRACT

An absorbent article includes a liquid-pervious sheet, an outer covering sheet, and an absorbent structure sandwiched between the liquid-pervious sheet and the outer covering sheet. The absorbent structure includes a liquid-absorbent mixture composed of super-absorbent polymer particles and fluff pulp and nonwoven fabric sheet formed from long fibers of thermoplastic resin. The nonwoven fabric sheet is put in contact, along at least one surface thereof, with the liquid-absorbent mixture and has cross points at which the long fiber sealed together, and a nap height defined by a difference between a thickness measured before a napping test and a thickness measured after the napping test is at least 0.5 mm.

10 Claims, 8 Drawing Sheets

ABSORBENT ARTICLE

RELATED APPLICATIONS

The present application is based on International Application Number PCT/JP2007/07177, filed Nov. 8, 2007 and claims priority from, Japanese Application Number 2006-335055, filed Dec. 12, 2006, the disclosures of which are hereby incorporated by reference herein in their entirety.

TECHNICAL FIELD

The present invention relates to an absorbent article.

RELATED ART

Absorbent articles such as disposable diapers or sanitary napkins have conventionally used an absorbent structure comprising a mixture of super-absorptive polymer particles and fluff pulp wrapped with tissue paper. In such absorbent structure, the super-absorptive polymer particles and fluff pulp (referred to hereinafter simply as liquid-absorbent mixture) have merely been mixed together, resulting in that the absorbent structure may be twisted or distorted and sometimes even get out of its desired shape due to movement of the wearer's body.

PATENT DOCUMENT 1 discloses the disposable wearing article wherein an absorbent panel (corresponding to the above-described absorbent structure) comprises an absorbent retention layer (corresponding to the above-described liquid-absorbent mixture) formed with a plurality of depressions sinking in a thickness direction and containing herein heat-sealable fibers and a nonwoven fabric layer placed on the upper surface of the absorbent retention layer and wherein the heat-sealable fibers contained in the absorbent retention layer and the nonwoven fabric layer are heat-sealed together along a contact surface between the absorbent retention layer and the nonwoven layer.

PATENT DOCUMENT 1: Japanese Unexamined Patent Application Publication No. 2002-11047 (claim 1 and FIG. 3)

DISCLOSURE OF THE INVENTION

Problems to be Solved by the Invention

In the disposable wearing article disclosed in the aforesaid PATENT DOCUMENT 1, even if the absorbent panel is deformed, the absorbent retention layer is well resistant against getting out of its desired shape since the heat-sealable fibers contained in the absorbent retention layer and the nonwoven fabric layer are heat-sealed together along the contact surface between the absorbent retention layer and the nonwoven fabric layer. However, it is anxious that a desired flexibility of the absorbent panel (corresponding to the above-described absorbent structure) might be deteriorated due to the heat-sealing of the heat-sealable fibers contained in the absorbent retention layer with the nonwoven fabric layer. Thus there is a need for further improvement.

In view of the problem left unsolved behind by the prior art, it is an object of the present invention to provide an absorbent article including a liquid-absorbent mixture well protected from the anxiety of getting out of its desired shape not at the cost of the flexibility of the liquid-absorbent mixture.

Measure to Solve the Problem

According to the present invention, there is provided an absorbent article comprising a liquid-pervious sheet, an outer covering sheet opposed to the liquid-pervious sheet, and an absorbent structure interposed between the liquid-pervious sheet and the outer covering sheet wherein the absorbent structure includes a liquid-absorbent mixture composed of super-absorbent polymer particles and fluff pulp and a non-woven fabric sheet formed from long fibers of thermoplastic resin.

The absorbent article further comprising the nonwoven fabric sheet being put in contact, along at least one surface thereof, with the liquid-absorbent mixture and having cross points at which the long fibers sealed together, and a nap height defined by a difference Tb-Ta between a thickness Ta measured before a napping test and a thickness Tb measured after the napping test is at least 0.5 mm.

It should be noted that details of "napping test" used herein will be described later.

According to one preferred embodiment of the present invention, the nonwoven fabric sheet is made by a spunbond process or melt blow process.

According to another preferred embodiment of the present invention, the nonwoven fabric sheet demonstrates a maximum load of 2.0 N/25 mm as measured by a tensile test conducted in a cross direction orthogonal to a machine direction.

According to still another preferred embodiment of the present invention, a ratio Eb/Ep of a tensile elongation at break Eb of the nonwoven fabric sheet as measured in the cross direction and a tensile elongation Ep causing a maximum load is at least 6.5.

According to yet another preferred embodiment of the present invention, the long fibers forming the nonwoven fabric sheet comprises at least one type of thermoplastic resin selected from a group consisting of polyethylene and ethylene copolymer.

According to further another preferred embodiment of the present invention, the long fibers forming the nonwoven fabric sheet is of a core-and-sheath type, the sheath of the long fibers is formed at least one type of thermoplastic resin selected from a group consisting of polyethlene and ethylene copolymer, and the core of the longer fibers contains thermoplastic resin having a melting point higher than that of thermoplastic resin forming the sheath.

Effect of the Invention

The absorbent structure included in the absorbent article according to the present invention comprises the nonwoven fabric sheet made from the long fibers and the liquid-absorbent mixture composed of super-absorbent polymer particles and fluff pulp and put in contact with the nonwoven fabric sheet wherein the nonwoven fabric sheet has a nap height defined by a difference between a thickness Ta before napping test and a thickness Tb after napping test, i.e., Tb−Ta is at least 0.5 mm.

The nonwoven fabric sheet having a potential nap height of at least 0.5 mm is adapted to be easily raised in a fuzzy state as the wearer's body moves. As a result, the nonwoven fabric sheet made of longer fibers has its fiber density reduced to broaden interfiber spaces sufficiently to receive a desired quantity of the liquid-absorbent mixture and to retain this therein. In this way, the absorbent article is provided, of which the liquid-absorbent mixture is adapted to be reliably protected against getting out of its initial shape. The nonwoven fabric sheet is merely put in contact with the liquid-absorbent mixture and not heat sealed together and therefore it is unlikely that a flexibility of the absorbent structure might be deteriorated.

The nonwoven fabric sheet of such long fibers is preferably formed by the spunbond process or the melt blow process.

The nonwoven fabric sheet having the maximum load of at least 2.0 N/25 mm as measured by the tensile test in the cross direction orthogonal to the machine direction is suitable as the nonwoven fabric sheet put in contact with the liquid-absorbent mixture since the sealed cross points of the long fibers are broken and readily napped as the wearer's body moves.

The nonwoven fabric sheet having a ratio of the tensile elongation at break Eb in the cross direction to the tensile elongation Ep causing the maximum load, i.e., Eb/Ep≧6.5 is easily napped and preferable as the nonwoven fabric sheet put in contact with the liquid-absorbent mixture.

The nonwoven fabric sheet preferably contains at least one type of thermoplastic resin selected from a group consisting of polyethylene and ethylene copolymer. In this way, the thermoplastic resin having suitable heat seal temperature and heat seal strength may be appropriately selected to adjust easily strength and elongation of the nonwoven fabric sheet.

Preferably, the long fibers forming the nonwoven fabric sheet is of core-and-sheath type wherein the sheath of the long fibers is formed by at least one type of thermoplastic resin selected from the group consisting of polyethylene and ethylene copolymer while the core of the long fibers contains thermoplastic resin having a melting point higher than the melting point of the thermoplastic resin forming the sheath. Use of such long fibers makes it possible to eliminate apprehension that the core might be fused during a process of heat sealing and a volume of the nonwoven fabric might be decreased due to the heat seal.

Figure 1:
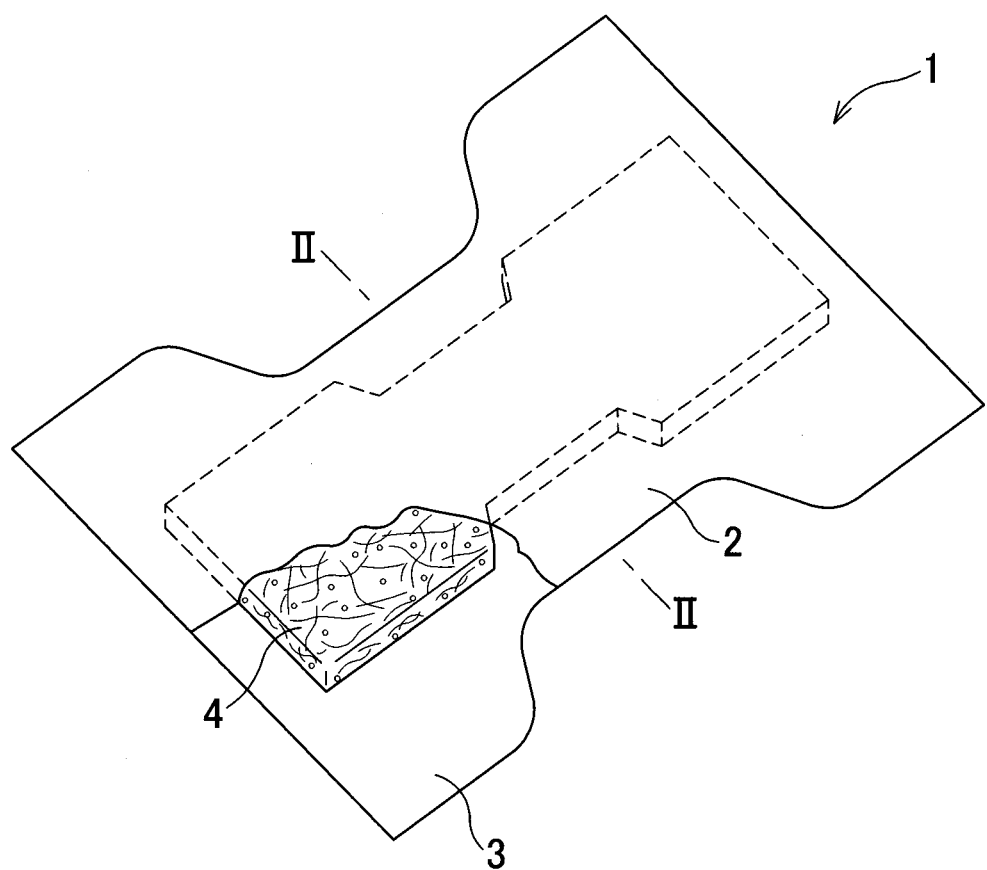
FIG. 1 is a partially cutaway perspective view showing a disposable diaper.

IDENTIFICATION OF REFERENCE NUMERALS USED IN THE DRAWINGS 1 diaper (absorbent article)
2 liquid-pervious sheet
3 outer covering sheet
4 absorbent unit
5 liquid-absorbent mixture
6 tissue paper
11 nonwoven fabric sheet
12 fluff pulp
13 super-absorbent polymer particles

DESCRIPTION OF THE BEST MODE FOR WORKING OF THE INVENTION

An absorbent article according to the present invention will be described in more details with reference to the accompanying drawings.

A disposable diaper 1 shown in FIG. 1 in a partially cutaway perspective view is a typical embodiment of the absorbent article according to the invention. The diaper 1 comprises a liquid-pervious sheet 2 adapted to come in contact with the wearer's skin, a liquid-impervious outer covering sheet 3 opposed to the liquid-pervious sheet 2 and an absorbent structure 4 sandwiched between these two sheets. Both the liquid-pervious sheet 2 and the outer covering sheet 3 dimensioned to be larger than the absorbent structure 4 are put flat together so as to encapsulate the absorbent structure 4 therebetween. The absorbent structure 4 is constricted in its longitudinally middle region so as to present a generally hourglass-like shape. The diaper 1 is provided with well known members such as elastic members serving to assure a fit of the diaper about the wearer' legs and waist and/or leak-barrier cuffs (not shown).

Figure 2:
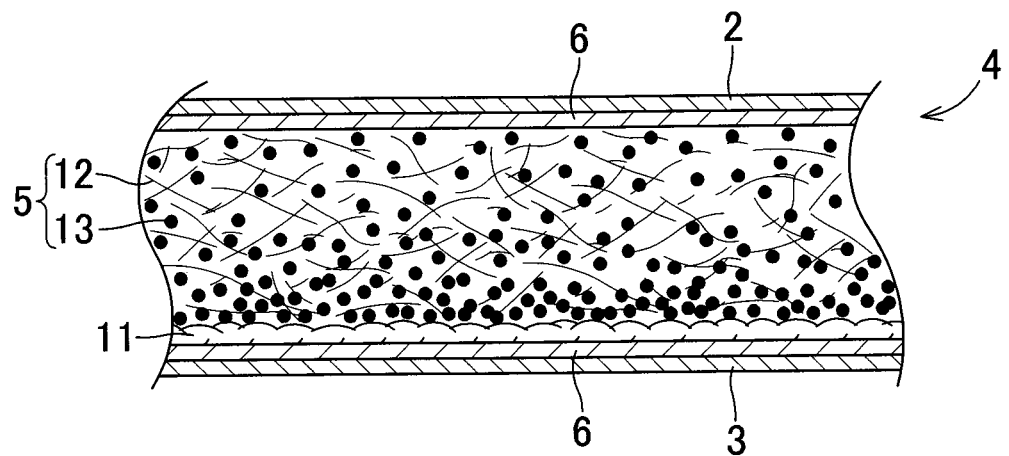
FIG. 2 is a sectional view taken along the line II-II in FIG. 1.

FIG. 2 is a sectional view of the absorbent structure 4 taken along a line II-II in FIG. 1. The absorbent structure 4 comprises a liquid-absorbent mixture 5 composed of fluff pulp 12 and super-absorbent polymer particles 13, and a nonwoven fabric sheet 11 made by long fibers of thermoplastic resin wherein the liquid-absorbent mixture 5 and the nonwoven fabric sheet 11 is wrapped with tissue paper 6.

The nonwoven fabric sheet 11 has one surface thereof put in contact with the liquid-absorbent mixture 5 and the other surface put in contact with the tissue paper 6. Both the liquid-pervious sheet 2 and the outer covering sheet 3 are also put in contact with the tissue paper 6. Boundary surfaces such as those between the nonwoven fabric sheet 11 and the liquid-absorbent mixture 5, between the nonwoven fabric sheet 11 and the tissue paper 6, and between the liquid-absorbent sheet 2 and the tissue paper 6 are intermittently coated with hot melt adhesives (not shown) and these paired components defining the respective boundary surfaces are bonded together.

The liquid-pervious sheet 2, the outer covering sheet 3, the fluff pulp 12, the super-absorbent polymer particles 13 and the hot melt adhesives may be those appropriately selected from the well known materials conventionally used for absorbent articles. Incidentally, the fluff pulp 12 used for the absorbent article may have a weight(mass)–average fiber length in the order of 3.1 mm and an average fiber diameter in the other of 40 μm while the super-absorbent polymer particle 13 may have a particle diameter in range of 0.1 to 0.8 mm and in a range of 0.3 to 0.5 mm for many of these particles 13.

The nonwoven fabric sheet 11 comprises a fibrous nonwoven fabric sheet made of thermoplastic resin long fibers bonded together at cross-points of the long fibers. A spunbond process or a melt-blow process not only facilitates the nonwoven fabric sheet to be made from long fibers but also facilitates the long fibers to be heat sealed at the cross points of the long fibers. From these viewpoints, the spunbond process or the melt-blow process is suitable for production of the nonwoven fabric sheet 11.

When the spunbond process or the melt-blow process is adopted to obtain the nonwoven fabric sheet 11, the thermoplastic resin constituting the nonwoven fabric sheet 11 preferably contains at least one selected from a group consisting of polyethylene and ethylene copolymer. More preferably, the long fibers forming the nonwoven fabric sheet has a core-and-sheath construction wherein the sheath is formed by thermoplastic resin selected from a group consisting of polyethylene and ethylene copolyer while the core is formed by a resin containing thermoplastic resin having a melting point higher than the sheath forming thermoplastic resin. Use of the thermoplastic resin having a high melting point as the sheath is effective to prevent a thickness of the nonwoven fabric sheet 11 from being unacceptably reduced when the nonwoven fabric sheet 11 is heated.

The group consisting of polyethylene and ethylene copolymer may be inclusive of low density polyethylene obtained by high-pressure process, ethylene-vinyl acetate copolymer (EVA), ethylene-acrylic ester or methacrylic acid copolymer, linear chain low density polyethylene obtained by ionic polymerization, medium density polyethylene and high density polyethylene. The high melting point thermoplastic resin used to constitute the sheath may be selected from a group including polypropylene, polyester and nylon.

The nonwoven fabric sheet 11 according to the invention is in a state appropriately raised to create naps of long fibers among which the liquid-absorbent mixture 5 is received and retained. In view of easiness for napping, the nonwoven fabric sheet 11 is preferably the one having interfiber heat seal strength sufficiently low to ensure that the heat sealed points are easily broken as the wearer's body moves, instead of so-called general-purpose nonwoven fabric sheets conventionally used for absorbent articles such as diapers.

Among various types of thermoplastic resin, polyethylene and ethylene copolymer (referred to hereinafter as polyethylene or the like) has a melting point sufficiently low to ensure that the long fiber is easily heat sealed at cross point thereof. Melting point and heat sealing temperature of polyethylene or the like may be appropriately selected to obtain a desired heat seal strength and, in this regard, such polyethylene or the like is suitable for use as raw materials for the nonwoven fabric sheet 11. At the same heat seal temperature, polyethylene or the like shows more noticeably than the other substances a general tendency that the heat seal strength is reduced as the melting point rises. The temperature optimal for heat seal of polyethylene or the like is a range 10 to 30° C. lower than the melting point thereof and, for the same polyethylene or the like, the heat seal strength can be reduced by setting the heat seal temperature to be lower than the optimal value. In view of this, for example, polyethylene or the like having a high melting point may be used or the temperature at which the heat sealing is carried out may be selected to be lower than the optimal value to reduce the heat seal strength and thereby to obtain the nonwoven fabric sheet 11 adapted to be readily napped.

A nonwoven fabric sheet having a nap height of 0.5 mm or more as a measuring method which will be described below is used for the present invention. The nap height less than 0.5 mm will make it impossible to receive a desired amount of the liquid-absorbent mixture 5 and to retain it as will be described in more details.

Measurement of the nap height was conducted on a test piece having its surface subjected to a friction treatment using Friction Tester AB-301 manufactured by TESTER SANGYO CO., LTD. in conformity with JIS L 0849. Thickness values of this test piece before and after subjected to the friction treatment were determined.

<Condition of Friction>

Figure 3:
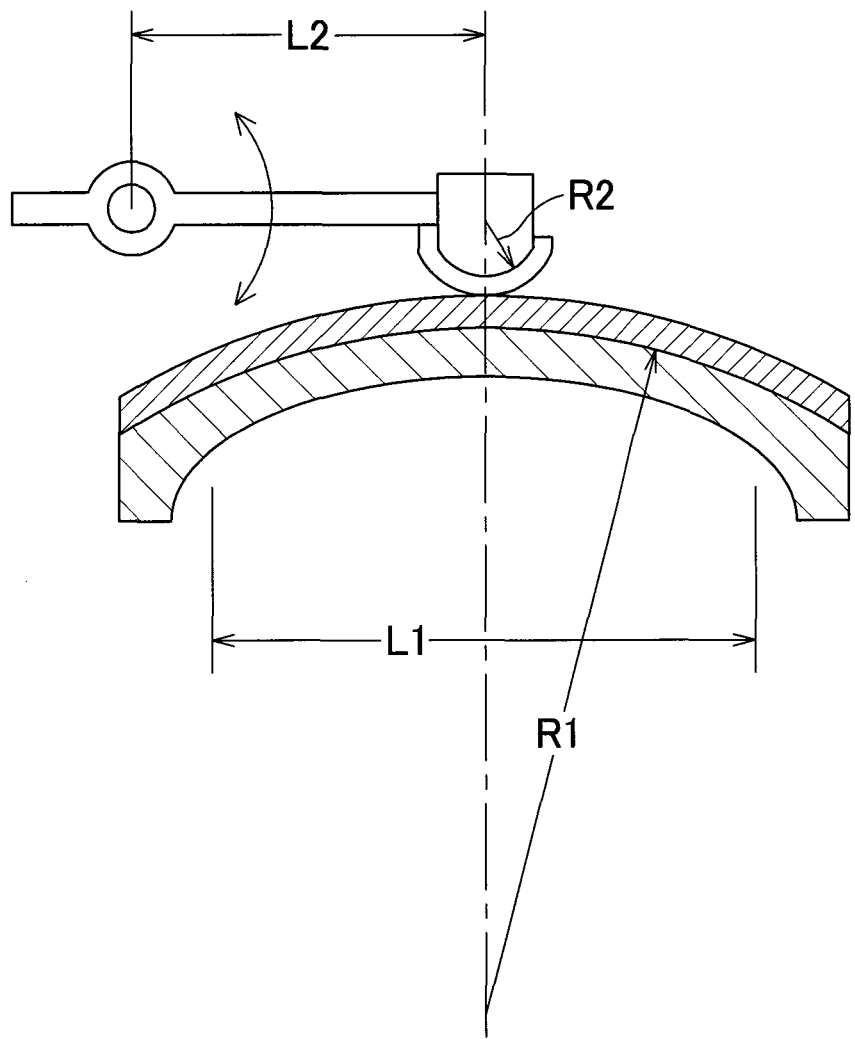
FIG. 3 is a schematic diagram illustrating a method of friction test.

As schematically illustrated in FIG. 3, the friction tester comprises a friction head having a radius R2 of 45 mm and a surface area of 20×20 mm, and a test piece support having a curvature radius R1=200 mm and fixed axis at a distance L2=110 mm from the friction head. Friction test was conducted by reciprocating the friction head 50 times on the condition of test load=200 gf (1.96 N), friction head's stroke L1=120 mm and reciprocating frequency=30/min.

The test piece was cut out from the nonwoven fabric sheet 11 in a rectangular shape dimensioned to be 140 mm in a direction in parallel to a machine direction (MD) during continuous production of the nonwoven fabric sheet 11 and to be 25 mm in a cross direction (CD) orthogonal to the machine direction. The friction test was conducted by subjecting the nonwoven fabric sheet 11 in MD direction.

The test piece support is made of esterified urethane while the friction head is made of stainless steel and adapted to be put in direct friction with the nonwoven fabric sheet 11.

<Method for Measuring Test Piece's Thickness>

Figure 4:
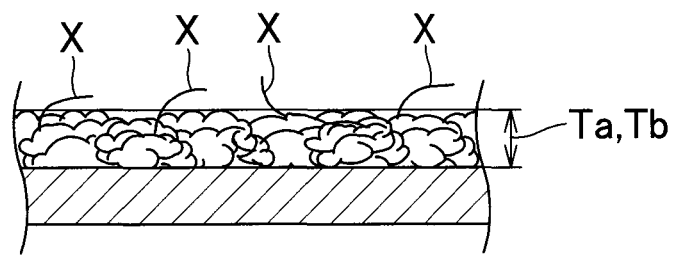
FIG. 4 is a schematic diagram illustrating a method for measuring thickness of nonwoven fabric sheet.

As a measuring instrument, Digital Microscope VHX-100 manufactured by KEYENCE CORPORATION was used wherein the test piece was fixed to a test piece fixing support by means of pressure-sensitive adhesive double coated tape with no load upon the test piece and laterally observed at 75 magnifications so that a distance from the test piece fixing support to the upper surface of the test piece can be measured on a monitor display as the thickness. In this measurement, several fibers X projecting from the upper surface of the test piece as illustrated by FIG. 4 were not involved in the thickness to be measured. A difference between the thickness Tb measured in the manner as has been described above under a frictional load and the thickness Ta measured in the manner as has been described above under no frictional load, i.e., Tb−Ta was obtained as the nap height.

In order to obtain the nonwoven fabric sheet 11 having a desired nap height, it is essential that the heat seal points should be broken under a force exerted upon the nonwoven fabric sheet 11 during use of the absorbent article. In order that the absorbent article can be produced in an industrial scale, on the other hand, it is essential that the nonwoven fabric sheet 11 should not be easily broken. To meet such contradictory requirements, the nonwoven fabric sheet 11 preferably has anisotropic property with respect to the tensile strength such that, in one direction, the tensile strength is sufficiently low to facilitate the nonwoven fabric sheet 11 to be readily broken at the heat seal points and, in the direction orthogonal to the first-mentioned direction, the tensile strength is sufficiently high to prevent the nonwoven fabric sheet 11 from being readily broken during the process for manufacturing the absorbent article. During the process for manufacturing of the nonwoven fabric sheet, the tensile strength thereof generally tends to be higher in the MD direction than in the CD direction. Utilizing such tendency, the manufacturing condition for the nonwoven fabric sheet 11 may be appropriately adjusted to meet those contradictory requirements.

In the case of the absorbent article implemented in the form of the diaper 1, force exerted upon the absorbent structure 4 due to the movement of the wearer's body is in the order of about 2.0 N/25 mm and therefore the maximum load used for the tensile test in the CD direction of the nonwoven fabric sheet 11 is preferably set to 2.0 N/25 mm or less.

The tensile strength of the nonwoven fabric sheet in the MD direction required for manufacturing depends on the particular manufacturing equipment. Generally, the break strength of 4.0 N/25 mm or higher, preferably 8.0 N/25 mm or higher is required.

The tensile test was conducted in a manner as follows:

From the test piece as has been described above, a test piece in the form of paper strip having a width of 25 mm and a length of 140 mm was cut. Tensile Tester of Model 5564 (load cell capacity of 50 N) manufactured by INSTRON CORPORATION was used to measure a load on the test condition: a distance of 100 mm between chucks used to hold the test piece and a tensile rate of 100 mm/min. A distance between the chucks of the tensile tester was determined as a tensile elongation.

EXAMPLES

Nonwoven fabric sheets corresponding to EXAMPLEs 1 through 3 as well as corresponding to CONTROLs 1 through 3 were manufactured and nap height measurement and tensile test was conducted on these EXAMPLEs and CONTROLs. In addition, diaper-type samples provided with the absorbent structures 4 comprising the respective nonwoven fabric sheets were manufactured to determine the preventive effect of the liquid-absorbent mixture 5 against getting out of its initial shape.

All the nonwoven fabric sheets prepared for the nap height measurement and the tensile test are common one to another in that the long fibers of core-and-sheath type with the core made of polypropylene (PP) was spunbond processed to form the nonwoven fabric which was, in turn, subjected to heat sealing by means of the same embossing die. As the long fibers constituting the sheath, various types of polyethylene (PE) having different melting points were used to vary the heat seal temperature and thereby to vary the heat seal strength. In this way, the nap height was appropriately adjusted. Fiber diameter of the long fibers was in a range of 20 to 25 μm.

As specifically indicated in TABLE 1, in EXAMPLE 1, PE having a melting point of 125° C. was used as material for the sheath to obtain a nonwoven fabric sheet having a mass of 30 g/m² and Shimadzu Corporation and a thickness of 0.2 mm. In EXAMPLE 2, a mass of nonwoven fabric sheet was one half of the mass of EXAMPLE 1 and the heat seal temperature was the same as that of EXAMPLE 1. In EXAMPLE 3, PE having a melting point of 132° C. was used as material for the sheath, and a nonwoven fabric sheet having a mass of 30 g/m² was obtained at a heat seal temperature 10° C. higher than in the case of EXAMPLE 1.

In CONTROLs 1 through 3, PE having a melting point of 124° C. was used as material for the sheath and nonwoven fabric sheets respectively having masses of 18, 20 and 30 g/m² were obtained at s heat seal temperature 10° C. higher than in the case of EXAMPLE 1. Melting points of PE was measured by DSC measuring instrument Model DSC-60 manufactured by Shimadzu Corporation at a temperature rising rate of 10° C./min.

The nonwoven fabric sheets as CONTROLs 1 through 3 were obtained at the heat seal temperature 10° C. higher than in the case of EXAMPLE 1 and commonly had the same quality as the general-purpose nonwoven fabric sheet conventionally used for the diaper.

On the nonwoven fabric sheets as EXAMPLEs 1 through 3 as well as the nonwoven fabric sheets as CONTROLs 1 through 3, the nap height Tb−Ta was measured using the method as has been described above. Result of this measurement is indicated by TABLE 1.

Now the effect of the nonwoven fabric sheet 11 to prevent the liquid-absorbent mixture 5 from getting out of its initial shape was evaluated by following a sequence as will be described below.

<Manufacturing of Diaper-Type Samples for Evaluation>

50% by mass of fluff pulp 12 and 50% by mass of super-absorbent polymer particles 13 were fed to a laboratory small size fibrillating machine to prepare the liquid-absorbent mixture 5 which was then accumulated on any one of the nonwoven fabric sheets as EXAMPLEs or CONTROLs until a mass of 440 g/m² and this laminate was wrapped with tissue paper 6 to obtain the absorbent structure 4 having a width of 270 mm and a length of 500 mm.

The fluff pulp 12 constituting the mixture 5 had a weight (mass)–average fiber length of 3.1 mm and a fiber diameter 40 μm. Particle diameter of the super-absorbent particles 12 was distributed in such pattern that 30% by mass thereof has a particle diameter in a range of 150 to 300 μm, 63% by mass thereof has a particle diameter in a range of 300 to 500 μm and 27% by mass has a particle diameter in a range of 500 to 710 μm. The same type of tissue paper 6 was used for all of EXAMPLEs and CONTROLs.

Then, the absorbent structure 4 was trimmed in the hour-glass-shape (See FIGS. 1 and 7) which was, in turn, sprayed once with water. This absorbent structure 4 was sandwiched between the rectangular liquid-pervious sheet 2 and the outer covering sheet 3 (See FIG. 1) the nonwoven fabric sheet 11 laid on the side of the outer covering sheet 3 and these components were bonded by means of hot melt adhesives. During operation of bonding, gauge pressure of 3 kg/cm² of a hydraulic press was exerted on the components. In this way, the diaper-type samples for evaluation were obtained. It should be noted here that the shape of the absorbent structure is not specified so far as a sample S having a length of 140 mm and a width of 65 mm as will be described later can be taken from the absorbent structure 4. A cushion sheet was sandwiched between the absorbent structure 4 and the liquid-pervious sheet 2.

This diaper-type sample was made using materials as follow:

Liquid-pervious sheet 2: air-through nonwoven fabric having a mass of 25 g/m²;

Outer covering sheet 3: air-permeable polyethylene film having a mass of 22 g/m²;

Cushion sheet: air-through nonwoven fabric having a mass of 40 g/m²;

Tissue paper: having mass of 18 g/m²;

Hot melt adhesive: application quantity of 5 g/m² (in spiral pattern)

<Measurement of Quantity of Liquid-Absorbent Mixture Retained By Nonwoven Fabric Sheet>

A test piece including the absorbent structure 4 cut from the diaper-type sample was subjected to the predetermined times of reciprocating friction using the above-described friction tester and then a quantity of the liquid-absorbent mixture retained by the nonwoven fabric sheet 11 was measured. Such measurement will be described below in more details.

Figure 5:
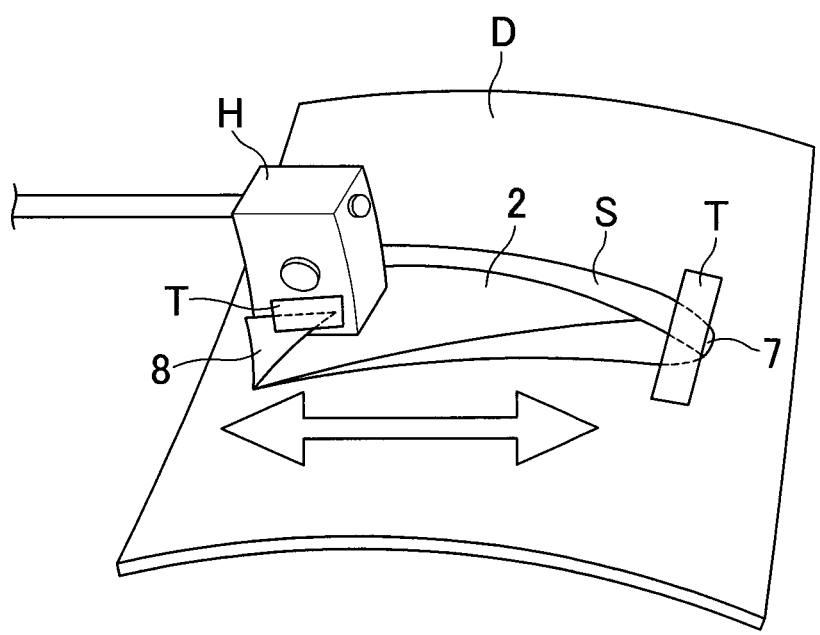
FIG. 5 is a schematic diagram illustrating a method for measuring a quantity of liquid-absorbent mixture retained in nonwoven fabric sheet.

From the region of the above-described diaper-type sample including the absorbent structure 4, a test piece S was cut so that a longitudinal direction of this sample is defined by the MD direction of the nonwoven fabric sheet 11 and this test piece S has a length of 140 mm and a width of 65 mm. As illustrated in FIG. 5, longitudinally one end 7 of the sample S was fixed to a test piece support D of the friction tester by means of pressure-sensitive adhesive tape T with the side of the liquid-pervious sheet 2 of this sample S facing upward.

After the friction head H has been placed on the sample S, the longitudinally other end 8 was fixed to the friction head H by means of pressure-sensitive adhesive tape T.

Now, with a load of 200 gf (1.96 N) and a stroke of 120 mm and reciprocating rate of 30 times/min, the friction head H was reciprocated in the longitudinal direction 30 times.

After completion of the friction test, a practical use of the article was simulated by pouring artificial urine of 20 cm$^3$ on a region of the sample S which had been rubbed by the friction head H. After one minute had elapsed, a test piece having a length of 120 mm and a width of 35 mm was cut around the region which had been rubbed by the friction head H. The artificial urine was prepared by adding 200 g of urea, 80 g of common salt, 8 g of magnesium sulfate, 3 g of calcium chloride and a spoonful (about 1 g) pigment Blue #1 to 10 l of ion-exchanged water.

The liquid-pervious sheet 2 and the outer covering sheet 3 of this test piece were pulled in opposite directions respectively gripped by fingers of both hands and pulled in opposite directions to tear the liquid-absorbent mixture 5 apart into its portion present on the side of the liquid-pervious sheet 2 and its portion present on the outer covering sheet 3.

After a mass Wa of the outer covering sheet 3 torn apart in this manner including the nonwoven fabric sheet 11, the liquid-absorbent mixture 5 and the tissue paper 6 was measured, the liquid-absorbent mixture 5 clinging to the outer covering sheet 3 was removed and a mass Wb of the outer covering sheet 3 devoid of the liquid-absorbent mixture 5 was measured.

In this measurement, the mass of the liquid-absorbent mixture 5 clinging to the outer covering sheet 3 include the mass thereof due to wetness and the mass thereof retained by the nappy nonwoven fabric 11. However, the part of the mass under the effect of wetness is substantially constant independently of nature of the nonwoven fabric sheet 11. In view of this, a difference between the mass Wa and the mass Wb was calculated as an apparent quantity of the liquid-absorbent mixture 5 retained by the nonwoven fabric sheet 11. Such apparent quantity of the liquid-absorbent mixture retained by the nonwoven fabric sheet 11 was calculated also for the test piece which had not been subjected to the friction test and thereby the apparent quantities of the liquid-absorbent mixture 5 retained by the nonwoven fabric layer 11 having been subjected to the friction test, i.e., having naps and by the nonwoven fabric sheet 11 having not been subjected to the friction test, i.e., having none of naps were comparatively determined.

With respect to EXAMPLEs and CONTROLs, the apparent quantity of the liquid-absorbent mixture 5 retained by the nonwoven fabric sheet and difference thereof depending on whether the nonwoven fabric sheet 11 had been friction tested or not, are indicated in TABLE 1. As will be apparent from TABLE 1, in EXAMPLEs 1 and 2 each having a PE melting point similar to those in CONTROLs 1 through 3 but having a relatively low heat sealing temperatures as well as in EXAMPLE 3 having a heat sealing temperature similar to those of CONTROLs 1 through 3 but having a relatively high PE melting point, a nap height Tb–Ta was as high as 0.5 mm or more. In EXAMPLEs 1 through 3 each having the nap height Tb–Ta of 0.5 mm or more, a differential apparent quantity of the liquid-absorbent mixture 5 is about 0.5 g or higher. Contrastingly, in CONTROLs 1 through 3 each having the nap height significantly smaller than those in EXAMPLEs 1 through 3, the differential apparent quantity of the liquid-absorbent mixture 5 is about 0.1 g or less. On the basis of the data indicated in TABLE 1, it is obvious that a capacity of the absorbent article according to the present invention to retain the liquid-absorbent mixture 5 can be effectively improved by employing the nonwoven fabric sheet 11 adapted to be readily napped.

TABLE 1

| | Mass g/m$^2$ | Core/Sheath | Melting point of PE °C. | Nap height of nonwoven fabric | | | Apparently retained quantity (g) of liquid-absorbent mixture | | |
|---|---|---|---|---|---|---|---|---|---|
| | | | | Ta mm | Tb mm | Tb—Ta mm | Before friction test | After friction test | Difference |
| EXAMPLE 1 | 30 | PP/PE | 125 | 0.2 | 1.1 | 0.9 | 0.47 | 0.95 | 0.48 |
| EXAMPLE 2 | 15 | PP/PE | 125 | 0.2 | 0.7 | 0.5 | 0.29 | 0.86 | 0.57 |
| EXAMPLE 3 | 30 | PP/PE | 132 | 0.2 | 1.5 | 1.3 | 0.51 | 0.98 | 0.47 |
| CONTROL 1 | 18 | PP/PE | 124 | 0.2 | 0.4 | 0.2 | 0.22 | 0.32 | 0.10 |
| CONTROL 2 | 20 | PP/PE | 124 | 0.2 | 0.4 | 0.2 | 0.24 | 0.33 | 0.11 |
| CONTROL 3 | 30 | PP/PE | 124 | 0.2 | 0.4 | 0.2 | 0.30 | 0.27 | −0.30 |

<Deformation Promoting Test for Liquid-Absorbent Mixture 5>

Then, the diaper-type samples according to EXAMPLE 1, CONTROL 3 and the diaper-type sample having the absorbent structure 4 containing no nonwoven fabric sheet (CONTROL 4) were used to conduct a deformation promoting test for the liquid-absorbent mixture 5 in a sequence as will be described below in details. Taking account of a fact that the liquid-absorbent mixture 5 easily gets out of its initial shape once the liquid-absorbent mixture 5 has absorbed body fluids or the like and has been brought in wet condition, a small quantity of artificial urine was previously poured thereto before the deformation promoting test. It should be understood that CONTROL 4 was made by using the same materials as those for the other EXAMPLES and CONTROLS except that the absorbent structure 4 in this CONTROL 4 was not provided with the nonwoven fabric sheet.

Figure 6A:
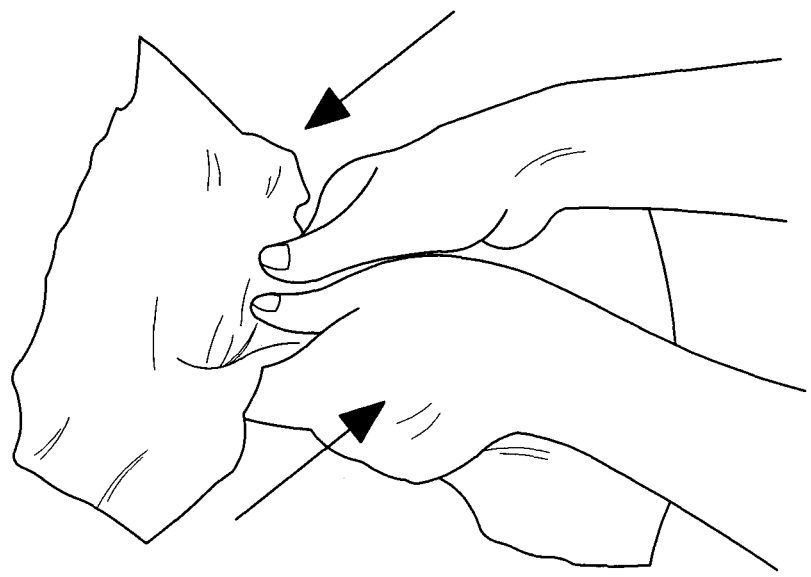
FIG. 6 is a schematic diagram illustrating a method for promoting deformation of the liquid-absorbent mixture.
Figure 6B:
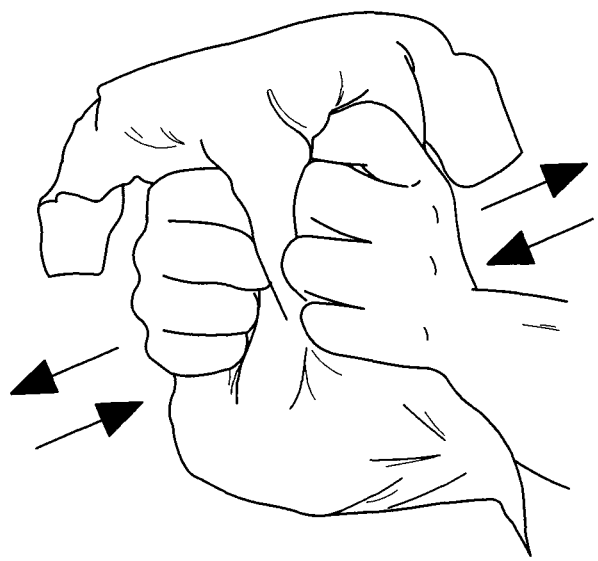

The deformation promoting test was started by pouring 40 cm$^3$ of artificial urine onto the diaper-type sample in the vicinity of a central region thereof for about 10 seconds and then the sample was left at rest. Thereafter, the region of the sample wetted with artificial urine was gripped by both hands. Then, the right and left hands gripping the sample were moved to pass each other in a back-and-forth direction ten (10) times as illustrated by FIG. 6A. Immediately thereafter, the right and left hands gripping the sample were moved towards and apart from each other in a cross direction ten (10) times as illustrated by FIG. 6B.

Figures 7A, 7B, 7C:
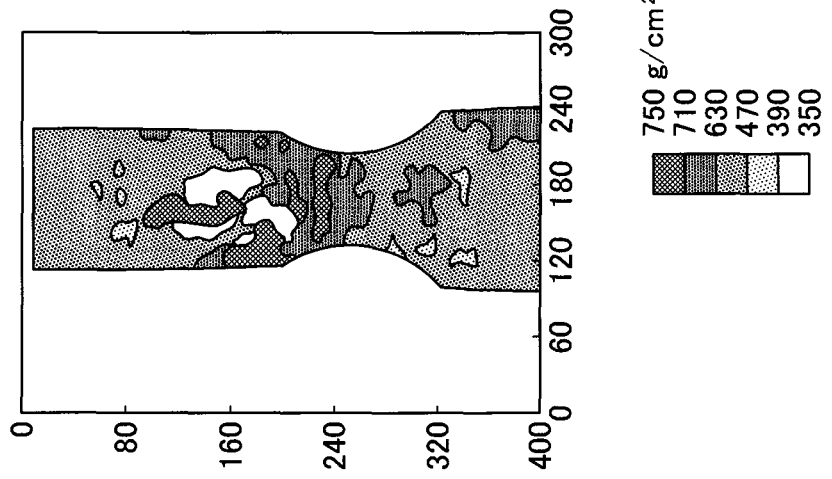
FIG. 7 is graphic diagram illustrating results of mass distribution measurement with respect to EXAMPLE 1 (in FIG. 7A), CONTROL 4 (in FIG. 7B) and CONTROL 1 (in FIG. 7C) respectively.

After the deformation promoting test, mass of the diaper-type sample was measured using X-ray-type thickness meter of Model PRF7X manufactured by Futec INC. The measurement was conducted on the diaper-type sample flatly mounted in a measuring frame at a scan pitch of 5 mm. Result of measurement is graphically illustrated by FIG. 7A through FIG. 7C. Specifically, FIG. 7A illustrates measurement result obtained on EXAMPLE 1, FIG. 7B illustrates measurement result obtained on CONTROL 4 and FIG. 7C illustrates measurement result obtained on CONTROL 1. The mass was represented in grey scale and, for example, a white area of the diaper-type sample represents an area in which a mass less than 350 g/m$^2$, more substantially, represents an area in which the liquid-absorbent mixture 5 is absent.

Comparison of these measurement results demonstrates that the mass of the diaper-type sample in the vicinity of its central region is relatively high and the liquid-absorbent mixture 5 having absorbed the artificial urine is present. In CONTROL 1 and CONTROL 4 (corresponding to FIG. 7C and FIG. 7B, respectively), the mass in the vicinity of the central region is substantially zero and it is demonstrated that the liquid-absorbent mixture 5 is substantially absent.

The measurement result demonstrates that the absorbent article according to the present invention is able to prevent the liquid-absorbent mixture 5 from getting out of its initial shape by providing the article with the nonwoven fabric 11 adapted to be easily napped.

Figure 8A:
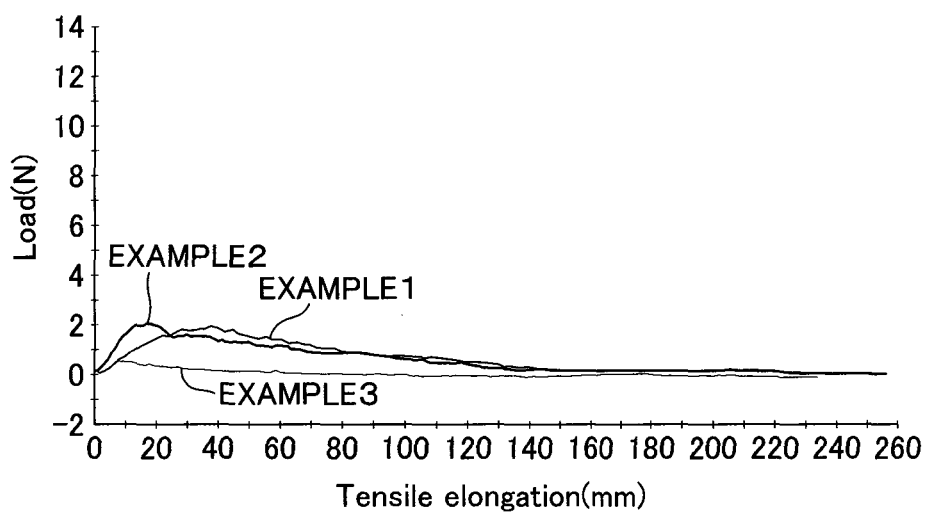
FIG. 8 is graphic diagram illustrating results of tensile test conducted in the CD direction with respect to EXAMPLEs 1 through 3 (in FIG. 8A) and CONTROLs 1 through 3 (in FIG. 8B), respectively.
Figure 8B:
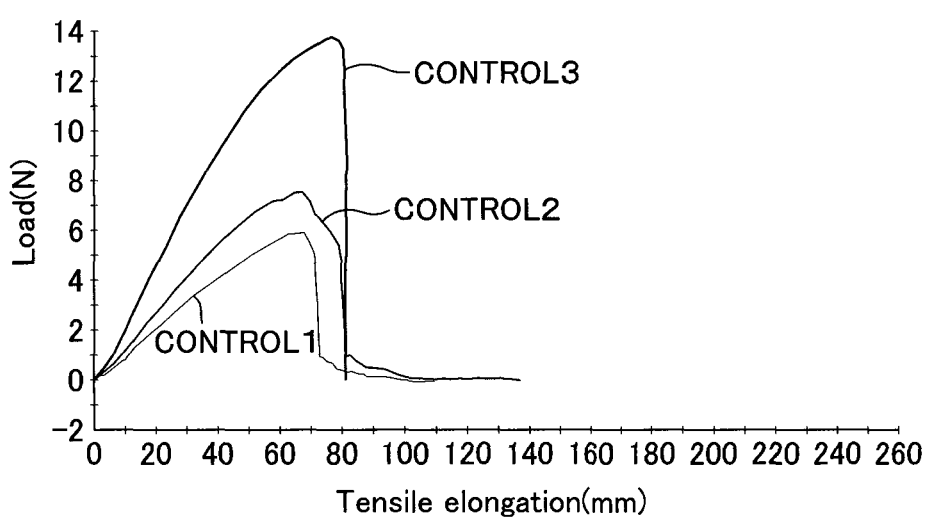
Figure 9A:
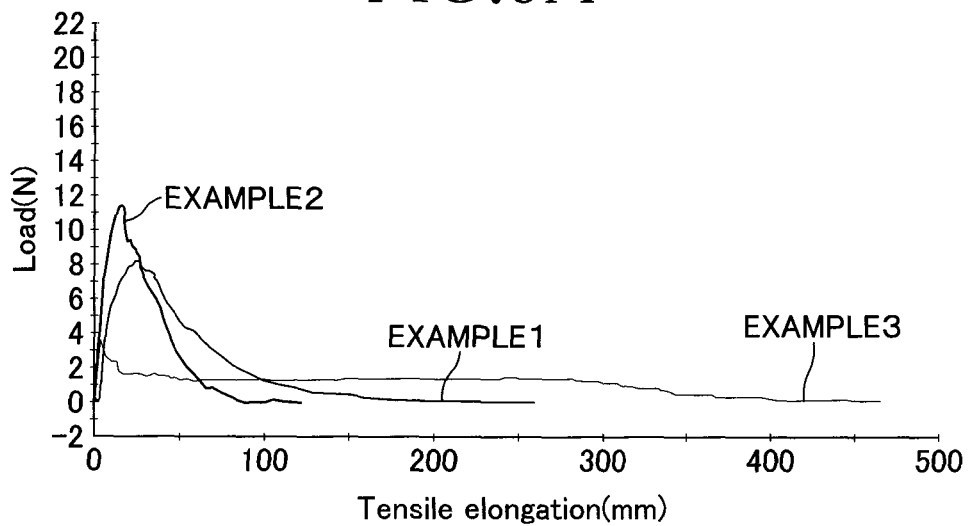
FIG. 9 is graphic diagram illustrating results of tensile test conducted in the MD direction with respect to EXAMPLEs 1 through 3 (in FIG. 9A) and CONTROLs 1 through 3 (in FIG. 9B), respectively.
Figure 9B:
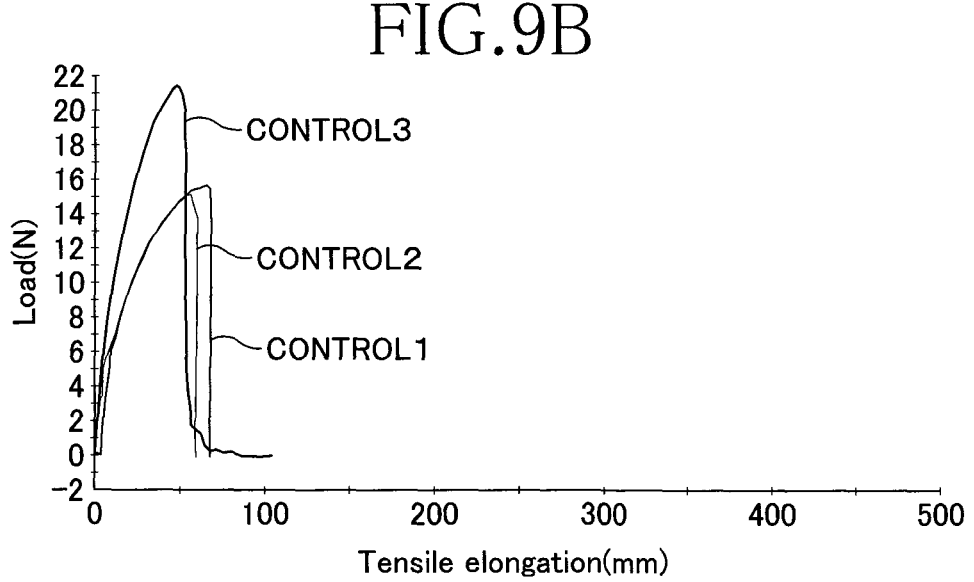

Now, using the measuring method as has been described above, the tensile test was conducted on the respective nonwoven fabric sheets according to EXAMPLEs as well as the respective nonwoven fabric sheets according to CONTROLs in the CD direction and the MD direction. The test result is indicated in TABLE 2 and graphically illustrated by FIGS. 8 and 9, wherein FIG. 8A illustrates the result of the tensile test conducted on EXAMPLEs 1 through 3, FIG. 8B illustrates the result of the tensile test conducted on CONTROLs 1 through 3 in the CD direction, FIG. 9A illustrates the result of the tensile test conducted on EXAMPLEs 1 through 3, and FIG. 9B illustrates the result of the tensile test conducted on CONTROLs 1 through 3 in the MD direction.

While the nonwoven fabric sheets according to EXAMPLEs 1 through 3 are similar to the general-purpose nonwoven fabric sheets according to CONTROLs 1 through 3 so far as increase of the tensile load at the initial stage, the formers demonstrate the maximum load Lp and a relatively high tensile elongation at break Eb with a relatively small elongation.

This is believed to be for the reason as follows: In the nonwoven fabric sheets according to EXAMPLEs 1 through 3, the heat seal strength at the cross points of the long fibers is lower than that in the general-purpose nonwoven fabric sheets and increase of load at the initial stage is substantially the same as in the general-purpose nonwoven fabric sheets. However, in the nonwoven fabric sheets according to EXAMPLEs reach the load causing the heat seal points to be broken with a lower elongation and thereafter the long fibers in crimped state are elongated until they are broken little by little. Consequentially, the long fibers should be further elongated until the nonwoven fabric sheets themselves are broken. In addition, the nonwoven fabric sheets are readily napped and ensure noticeable nap hights Tb−Ta since the heat seal points are broken at relatively low load and relatively small elongation.

Contrastingly, in the general-purpose nonwoven fabric sheets according to CONTROLs, the heat seal strength at the cross points of the long fiber are higher than those in EXAMPLEs and correspondingly the cross points are not broken until a higher tensile load is reached. However, once the load has attained to the maximum level Lp, the heat seal point and the long fiber itself are concurrently broken and thereupon the load suddenly decreases. It is believed to be for this reason that the nonwoven fabric sheets may be broken with a relatively low elongation.

TABLE 2

|  | Mass g/m$^2$ | Core/ Sheach | CD | | | | MD | | | |
| --- | --- | --- | --- | --- | --- | --- | --- | --- | --- | --- |
|  |  |  | Eb mm | Ep mm | Eb/Ep (—) | Lp N/25 mm | Eb mm | Ep mm | Eb/Ep (—) | N/25 mm |
| EXAMPLE 1 | 30 | PP/PE | 260 | 40 | 6.5 | 2.0 | 260 | 30 | 8.3 | 8.0 |
| EXAMPLE 2 | 15 | PP/PE | 235 | 15 | 16 | 2.0 | 120 | 15 | 8.0 | 11 |
| EXAMPLE 3 | 30 | PP/PE | 140 | 8.0 | 18 | 0.5 | 460 | 5 | 92 | 4.0 |
| CONTROL 1 | 18 | PP/PE | 110 | 68 | 1.6 | 6.0 | 61 | 60 | 1.0 | 16 |
| CONTROL 2 | 20 | PP/PE | 140 | 65 | 2.1 | 8.0 | 60 | 55 | 1.1 | 15 |
| CONTROL 3 | 30 | PP/PE | 81 | 80 | 1.0 | 14 | 55 | 50 | 1.1 | 21 |

As will be apparent from FIG. 8A and TABLE 2, in the case of the nonwoven fabric sheets according to EXAMPLEs 1 through 3, respectively, the tensile elongation Ep resulting in the maximum load Lp during the tensile test conducted in the CD direction was 40 mm or less and a tensile load slowly decreased as the test piece was further elongated. When the tensile elongation exceeded 140 mm, the load decreased substantially down to zero and the test piece was broken. The maximum load Lp was 2.0 N/25 mm or less.

While the similar tendency was observed in the MD direction, the maximum load Lp was higher than in the CD direction and specifically 4.0 N/25 mm or higher.

In the case of general-purpose type nonwoven fabric sheets according to CONTROLs 1 through 3, the tensile elongation Ep resulting in the maximum load Lp in the CD direction was 60 mm or higher and a tensile load drastically decreased as the tensile elongation at break Eb as the test piece was further elongated and the test piece was broken as this tensile elongation at break Eb was reached. The maximum Lp was 6.0 N/25 mm or higher.

To support the presumption as has been described above, the ratio Eb/Ep of the tensile elongation at break Eb in the CD direction to the tensile elongation Ep causing the maximum load Lp in the CD direction were calculated on the nonwoven fabric sheets according to EXAMPLEs 1 through 3 and on the general-purpose nonwoven fabric sheets according to CONTROLs, respectively. As will be apparent from TABLE 2 indicating the comparison result, the ratio Eb/Ep was 6.5 or higher in EXAMPLES 1 through 3 and 2.1 or lower in the general-purpose nonwoven fabric sheets.

In the MD direction, the ratio Eb/Ep in EXAMPLEs 1 through 3 was 8.0 or higher and 1.1 or lower in the general-purpose nonwoven fabric sheets.

As will be obviously understood from the foregoing description, the nonwoven fabric sheet suitable for the absorbent article according to the present invention is primarily characterized in an advantageously high value of Eb/Ep.

Furthermore, the nonwoven fabric sheets according to EXAMPLEs 1 through 3 are characterized by anisotropy in the tensile strength. More specifically, the maximum load Lp in the CD direction is 2.0 N/25 mm or lower while the maximum load Lp in the MD direction is 4.0 N/25 mm or higher. Thus the easiness for napping and the tensile strength required for efficient production are simultaneously met. While the present invention has been described on the basis of the particular embodiments, the present invention should not be construed to be limited by these embodiments but may be implemented in the other various manners. For example, the present invention is applicable not only to the diaper which has been exemplarily described above but also to other absorbent articles such as sanitary articles, e.g., sanitary napkins or pet articles, which uses an absorbent structure comprising super-absorbent polymer particles and fluff pulp. While the case in which one surface of the single nonwoven fabric sheet 11 is put in contact with the liquid-absorbent mixture 5 has been exemplarily described, it is possible without departing from the scope of the invention to sandwich the single nonwoven fabric sheet 11 between two layers of the liquid-absorbent mixture 5 so that the opposite surfaces of the nonwoven fabric sheet 11 are put in contact with the liquid-absorbent mixture 5. It is also possible without departing from the scope of the invention to divide the single nonwoven fabric sheet 11 into two or three sections. Furthermore, it is also possible to wrap the liquid-absorbent mixture 5 with the nonwoven fabric sheet 11 or to pleat the nonwoven fabric sheet 11 and thereby to enlarge the area of the nonwoven fabric 11 put in contact with the liquid-absorbent mixture 5.

The invention claimed is:

1. An absorbent article, comprising:
a liquid-pervious sheet;
an outer covering sheet facing said liquid-pervious sheet;
an absorbent structure sandwiched between said liquid-pervious sheet and said outer covering sheet,
said absorbent structure includes
a liquid-absorbent mixture including super-absorbent polymer particles and fluff pulp, and
a nonwoven fabric sheet including thermoplastic resin fibers which are bonded together at a cross-points thereof;
said nonwoven fabric sheet has naps in direct contact with said liquid-absorbent mixture without direct bonding to the liquid-absorbent mixture,
a nap height of the naps defined by a difference between a first thickness of the naps measured before a napping test and a second thickness of the naps measured after the napping test is at least 0.5 mm, and
the naps of the nonwoven fabric sheet are below the liquid-absorbent mixture.

2. The absorbent article according to claim 1, wherein said nonwoven fabric sheet is a spunbond or a melt-blown nonwoven fabric.

3. The absorbent article according to claim 1, wherein said nonwoven fabric sheet is configured to demonstrate a maximum load of 2.0 N/25 mm as measured by a tensile test conducted in a cross direction orthogonal to a machine direction.

4. The absorbent article according to claim 3, wherein a ratio of a tensile elongation at break of said nonwoven fabric sheet as measured in said cross direction and a tensile elongation caused by said maximum load is at least 6.5.

5. The absorbent article according to claim 1, wherein the fibers of said nonwoven fabric sheet comprise at least one selected from the group consisting of polyethylene and ethylene copolymer.

6. The absorbent article according to claim 1, wherein:
said fibers of said nonwoven fabric sheet has a core and a sheath;
the thermoplastic resin of said sheath includes at least one selected from the group consisting of polyethlene and ethylene copolymer; and
the thermoplastic resin of said core has a melting point higher than that of the thermoplastic resin of said sheath.

7. The absorbent article according to claim 1, wherein a tensile strength of the nonwoven fabric sheet in a first direction is lower than that in a second direction which is orthogonal to the first direction.

8. The absorbent article according to claim 1, wherein the naps are raised fibers of the nonwoven fabric sheet and the liquid-absorbent mixture is received and retained among the naps.

9. The absorbent article according to claim 7, wherein the tensile strength of the nonwoven fabric sheet is defined in a tensile test conducted in the first direction which is a cross direction orthogonal to the second direction which is a machine direction.

10. An absorbent article, comprising:
a liquid-pervious sheet;
an outer covering sheet facing said liquid-pervious sheet;
an absorbent structure sandwiched between said liquid-pervious sheet and said outer covering sheet,
said absorbent structure includes
a liquid-absorbent mixture including super-absorbent polymer particles and fluff pulp, and
a nonwoven fabric sheet including thermoplastic resin fibers which are bonded together at a cross-points thereof;
said nonwoven fabric sheet has naps in direct contact with said liquid-absorbent mixture without direct bonding to the liquid-absorbent mixture, and
the naps are between the liquid-absorbent mixture and the outer covering sheet.

* * * * *